(12) United States Patent
Hornung et al.

(10) Patent No.: US 11,226,300 B2
(45) Date of Patent: Jan. 18, 2022

(54) DETERMINATION OF FLUID PARAMETERS (71) Applicant: Sensirion AG, Stäfa (CH)

(72) Inventors: Mark Hornung, Stäfa (CH); Andreas Rüegg, Stäfa (CH)

(73) Assignee: Sensirion AG, Stäfa (CH)

( * ) Notice: Subject to any disclaimer, the term of this patent is extended or adjusted under 35 U.S.C. 154(b) by 1037 days.

(21) Appl. No.: 15/555,433

(22) PCT Filed: Mar. 5, 2015

(86) PCT No.: PCT/EP2015/054648
§ 371 (c)(1),
(2) Date: Sep. 1, 2017

(87) PCT Pub. No.: WO2015/075278
PCT Pub. Date: May 28, 2015

(65) Prior Publication Data
US 2018/0038811 A1 Feb. 8, 2018

(51) Int. Cl.
*G01N 25/20* (2006.01)
*G01N 33/22* (2006.01)
*G01N 25/00* (2006.01)

(52) U.S. Cl.
CPC .......... *G01N 25/20* (2013.01); *G01N 25/005* (2013.01); *G01N 33/225* (2013.01)

(58) Field of Classification Search
CPC .................................................... G01N 25/20
See application file for complete search history.

(56) References Cited

U.S. PATENT DOCUMENTS 4,384,792 A 5/1983 Sommers et al.
5,486,107 A 1/1996 Bonne
(Continued)

FOREIGN PATENT DOCUMENTS

AU 67191/00 A1 4/2001
DE 29 28 739 C2 3/1981
(Continued)

OTHER PUBLICATIONS

International Search Report and Written Opinion dated Apr. 7, 2015 in PCT/EP2015/054648 (9 pgs.).
(Continued)

*Primary Examiner* — John E Breene
*Assistant Examiner* — Jeffrey C Morgan
(74) *Attorney, Agent, or Firm* — Foley & Lardner LLP (57) ABSTRACT

A method for determining fluid parameters, such as a heat capacity $c_P\rho$, a calorific value Hp, a methane number MN, and/or a Wobbe index WI, of an unknown fluid (g). An unknown flow (55) of the fluid (g) is set in a sensor device (10), the sensor device (10) comprising a thermal flow sensor (1) and a pressure sensor device (15) for measuring at least one temperature value $T_1$, $T_2$, a further parameter, and differential pressure value $\Delta p$ over a flow restrictor (14). Using these measurement parameters $T_1$, $T_2$, $\Delta p$ and calibration data, the calorific value Hp, and/or the Wobbe index WI, or parameters indicative thereof, of an unknown fluid (g) are calculated. The invention also relates to such a sensor device (10) and to a computer program product for carrying out such a method.

18 Claims, 5 Drawing Sheets

(56) References Cited

U.S. PATENT DOCUMENTS

| | | | |
|---|---|---|---|
| 6,634,214 | B1 | 10/2003 | Thurston et al. |
| 7,188,519 | B2 | 3/2007 | Hornung et al. |
| 2004/0195531 | A1 | 10/2004 | Rahmouni et al. |
| 2006/0123892 | A1* | 6/2006 | Brekelmans .......... G01F 1/6847 73/61.76 |
| 2014/0345363 | A1 | 11/2014 | Pretre et al. |

FOREIGN PATENT DOCUMENTS

| | | |
|---|---|---|
| DE | 41 18 781 A1 | 12/1992 |
| DE | 10122039 A1 | 11/2002 |
| DE | 10122039 B4 | 11/2002 |
| EP | 0 554 095 A2 | 8/1993 |
| EP | 1 411 355 A1 | 10/2002 |
| EP | 1 265 068 A1 | 12/2002 |
| EP | 1 426 740 A2 | 10/2003 |
| EP | 2 015 056 A1 | 1/2009 |
| EP | 2 574 918 A1 | 4/2013 |
| EP | 2 806 271 A1 | 11/2014 |
| WO | WO-93/08457 A1 | 4/1993 |
| WO | WO-01/18500 A1 | 3/2001 |
| WO | WO-01/98736 A1 | 12/2001 |

OTHER PUBLICATIONS

Product Information for Portable Natural Gas Chromatograph Model 2928, Ametek Process Instruments, 2016 (2 pgs.).

User Manual for CWD 2005 Combustion Calorimeter for high speed measurement of fuel gases, Union Instruments GmbH, 2015, 121 pgs.

* cited by examiner

DETERMINATION OF FLUID PARAMETERS

CROSS REFERENCE TO RELATED APPLICATIONS

This application is a national stage entry of International Application No. PCT/EP2015/054648 filed Mar. 5, 2015; the disclosure of which is incorporated by reference herein in its entirety.

TECHNICAL FIELD

The present invention relates to a method for determining fluid parameters of an unknown fluid, in particular a calorific value of the fluid or a parameter related thereto, the fluid being preferably a burnable gas. It further relates to a measurement device and a computer program product configured to carry out said method.

PRIOR ART

Today's natural gas pipelines are organized in vast networks fed by numerous feed-in stations. As the gas in the pipeline system originates from different gas sources, the gas is naturally a mixture that varies over time.

A calorific value of the natural gas is an important technical and economic fluid parameter that is commonly determined by analysis of the gas composition. The gas composition may be measured by means of a gas chromatograph. Such devices are, however, expensive in acquisition as well as in maintenance. Moreover, measurement times are long and consequently, the measurement data are not available in real time but has to be gathered intermittently.

A further device for determining the calorific value of a natural gas is known from DE 101 22 039 A1. This document suggests using a gas flow meter with two temperature sensors and a heater arranged therebetween. From the two measured temperature values the calorific value of the natural gas is determined by linear interpolation. This method is, however, not as precise as desired. Moreover, a gas flow has to be kept constant during the measurement.

SUMMARY OF THE INVENTION

It is an object of the present invention to provide an improved method for determining a parameter of an unknown fluid. In particular, the method may be for measurement of a burnable gas or a mixture of such gases, in particular a natural gas of a mixture thereof, wherein the fluid parameter may be the calorific value of the fluid or a parameter indicative thereof.

This object is achieved by the method according to claim 1. Accordingly, a method for determining a characteristic parameter, in particular a calorific value $H\rho$ or a parameter indicative thereof, of an unknown fluid g, the unknown fluid g preferably being a burnable gas, preferably a natural gas, said fluid g flowing in a fluid flow through a sensor device, the sensor device comprising:

- a thermal flow sensor device with a heater element and at least one temperature element, preferably first and second temperature sensors, wherein the heater element is arranged between first and second temperature sensors,
- a flow restrictor arranged between first and second positions in said fluid flow, and
- a pressure sensor device for determining a pressure difference $\Delta p$ in the fluid g between said first and second positions, is suggested, the method comprising:

(i) establishing the fluid flow with an unknown value through said sensor device with at least part of the fluid g overflowing said thermal flow sensor;

(ii) activating the heating element of said thermal flow sensor and measuring at least one first temperature $T_1$ with said first temperature sensor and at least one second temperature $T_2$ with said second temperature sensor;

(iii) measuring first and second absolute pressures $p_1$, $p_2$ in the fluid g at the first and second positions, respectively, or measuring a differential pressure $\Delta p$ in the fluid g between the first and second positions with said pressure sensor device; and (iv) determining from the measured first and second temperatures $T_1$, $T_2$ and the measured pressure value(s) $\Delta p$ or $p_1$, $p_2$, a heat capacity $c_F\rho$, a calorific value $H\rho$ or a parameter indicative thereof, a methane number (MN) or a parameter indicative thereof, and/or a Wobbe index WI or a parameter indicative thereof, of the fluid g with correlation functions.

The term "fluid" relates in particular to gases, preferably burnable gases such as, e.g. natural gases, biogases, shell gases, town gases, or mixtures thereof or the like.

The methane number MN and the Wobbe index WI linearly correlate with one another.

Accordingly, the invention is based on the insight, that with two sensors, in particular a thermal flow sensor and a pressure sensor, parameters of an unknown fluid related to an energy content, in particular related to a calorific value, may be determined simply and effectively. Moreover, the present invention allows providing online (i.e. real-time) data. Accordingly, a fluid feed into a target device may be analyzed (and controlled) during the feed-in process.

In some embodiments, the method further comprises the step of:

(v) determining from the measured first and second temperatures $T_1$, $T_2$ a first characteristic parameter of the fluid g;

(vi) determining from the measured first and second temperatures $T_1$, $T_2$ and the measured pressure value(s) $\Delta p$ or $p_1$, $p_2$ a second characteristic parameter of the fluid g, wherein the second characteristic parameter contains additional information of the fluid g with respect to said first characteristic parameter;

(vii) determining from said first and second characteristic parameters the heat capacity $c_F\rho$, the calorific value $H\rho$ or a parameter indicative thereof, and/or the Wobbe index WI or a parameter indicative thereof, of the fluid g with the correlation functions.

Preferably, the first characteristic parameter of the fluid g is a heat conductivity $\lambda$ of said fluid g and the second characteristic parameter of said fluid g is a microscopic force $\xi$ of said fluid g.

It is to be understood that instead of two temperature sensors the heater element may also be designed to provide alternative parameters, such as one temperature and one heater current strength or the like such that at least two parameters that are indicative of first and second temperatures $T_1$, $T_2$ are available. In some embodiments, first calibration data and second calibration data are used that comprise first and second temperatures $T_1$, $T_2$ and the pressure value(s) $\Delta p$ or $p_1$, $p_2$ for at least one, preferably for two of more calibration fluids $g_1$, $g_2$. Accordingly, the sensor device according to invention may be calibrated with at least one, preferably two or more fluids. Preferably, said fluids do have characteristic parameters which are not too different from the characteristic parameters of the unknown fluid. The characteristic parameters of the calibration fluid may be within a range i.e. if λ is in the range with a lower bound of 50% to 300%, preferably 80% to 150%, more preferably 80% to 120% of the characteristic parameters of the calibration fluid.

The first calibration data may be data related to the first characteristic parameter, the second calibration data may be data related to the second characteristic parameter.

Preferably, the first and second calibration data is stored in at least one lookup table.

In some embodiments, said first characteristic parameter and said second characteristic parameter are determined by interpolation, preferably by linear interpolation. Accordingly, the calibration fluid(s) may be chosen such that an interpolation, preferably a linear interpolation, is possible.

Preferably, the second characteristic parameter is determined by resealing at least part of the relevant calibration data, particularly the second calibration data, prior to interpolation.

In some embodiments, the first calibration data further the heat conductivity $\lambda^{g1}$, $\lambda^{g2}$ of the calibration fluid $g_1$, $g_2$ and the second calibration data comprise the microscopic force $\tau^{g1}$, $\xi^{g2}$ of the calibration fluid $g_1$, $g_2$.

In some embodiments, the correlation functions are based on a quadratic Ansatz. Any coefficient of the correlation functions may be determined empirically, i.e. one uses available data of similar fluids, i.e. fluid with similar parameters (e.g. natural gases or mixtures thereof), and uses fitting techniques such as the least square method to determine the coefficients. Data sets for fluids are readily available in literature and publicly accessible data bases.

In some embodiments, the method further comprises:

(viii) determining a volume flow Q of the fluid flow of the fluid g from the heat capacity $c_P\rho$ and the heat conductivity λ. This may be done by the following equation:

$$Q = \frac{\lambda}{c_P\rho} F_\lambda^{-1}(\Theta_1).$$

Here, the function $\Theta_1 = F_\lambda(\phi_Q)$ denotes the flow signal of the thermal flow sensor as function of $$\phi_Q = \frac{c_P\rho}{\lambda} Q.$$

If λ is close enough to $\lambda^{g1}$ and $\lambda^{g2}$, the function $F_\lambda(\phi_Q)$ may be obtained by linearly interpolating the calibration data, as shown in Eqs. (9) and (10). The term "close enough" is explained below. Since, with the method according to invention, the parameters may be determined more precisely, also the heat capacity $c_P\rho$ may be determined more precisely. As the volume flow Q strongly depend on the heat capacity $c_P\rho$, the method according to invention also allows for determining the volume flow Q more precisely and without knowing the fluid, e.g. the gas sort, i.e. whether its propane or the like.

In some embodiments, the method further comprises:

(ix) determining an energy transfer per time unit from said volume flow Q and the calorific value Hρ of the fluid g. Accordingly, the sensor device according to invention may be operated as an energy meter, which may help to optimize a combustion process in a combustor.

Preferably, the method also comprises:

(x) outputting the heat capacity $c_P\rho$, the calorific value H, and/or the Wobbe index WI or the methane number MN. Any other parameter determined by means of the sensor device may be outputted on a display or the like or made available to further circuitry using said parameter, e.g. a combustion engine may use the calorific value or methane number determined in online measurements to control the volume flow Q of the fluid into the combustion zone or to control the combustion process itself.

Preferably, said method is carried out with the fluid g being a natural gas or a mixture thereof. This is advantageous as natural gases are widely known, i.e. one can find details data sets about their properties, and it is widely used, e.g. in combustion processes. Accordingly, there is a significant demand for small, inexpensive, and reliable devices for online measurements of natural gas flows.

It is another object of the present invention to provide a sensor device that is configured to carry out a determination of the calorific value of an unknown fluid or of a fluid parameter indicative thereof.

This object is achieved by a sensor device according to claim 11. Accordingly, a sensor device for measuring a heat capacity $c_P\rho$, a calorific value Hρ, methane number MN and/or a Wobbe index WI of a fluid g, or a parameter indicative of any one thereof, is suggested, the sensor device comprising:

a flow channel for the fluid g, the flow channel having an inlet and an outlet for the fluid g, a thermal flow sensor device with a heater element arranged between first and second temperature sensors, a flow restrictor arranged between first and second positions in said flow channel, at least one pressure sensor device for determining a pressure difference Δp in the fluid g between said first and second positions, and a digital control circuit comprising a memory, wherein the digital control circuit is configured to carry out a method according to invention.

In some embodiments, a memory stores the first and second calibration data, wherein the digital control circuit is configured to retrieve the first and second calibration data from said memory and to determine the first and second characteristic parameter, wherein, preferably, the correlations functions are stored in said memory and the digital control circuit is preferably configured to determine the heat capacity $c_P\rho$, the calorific value Hρ or a parameter indicative thereof, and/or a Wobbe index WI, a methane number MN or a parameter indicative thereof, of the fluid g with said correlation functions.

In some embodiments, the thermal flow sensor device is a CMOS flow sensor. This allows a particularly compact and cost efficient design of the device.

It is another object of the present invention to provide a computer program that, when carried out in a processor of a sensor device, carries out a determination of a calorific value of an unknown fluid or of a fluid parameter indicative thereof.

This object is achieved by a computer program according to claim 15. Accordingly, a computer program is provided that comprises computer program code that, when carried out in a digital control circuit of a sensor device according to invention, causes the digital control circuit to carry out a method according to invention.

Accordingly, in yet another aspect, the present invention provides a computer program product comprising computer program code that, when carried out in a processor of a digital control circuit of a sensor device, the sensor device comprising a thermal flow sensor device with a heater element arranged between first and second temperature sensors, a flow restrictor arranged between first and second positions in said fluid flow, and at least one pressure sensor device for determining a pressure difference Δp in the fluid g between said first and second positions, causes the digital control circuit to carry out any of the methods as described above, in particular, a method comprising:

(i) establishing an unknown flow of the fluid g through the sensor device with at least part of the fluid g overflowing said thermal flow sensor;

(ii) activating the heating element of the thermal flow sensor and measuring at least one first temperature $T_1$ with said first temperature sensor and at least one second temperature $T_2$ with said second temperature sensor;

(iii) measuring first and second absolute pressures $p_1$, $p_2$ in the fluid g at the first and second positions, respectively, or a differential pressure Δp in the fluid g between the first and second positions with said pressure sensor device; and (iv) determining from the measured first and second temperatures $T_1$, $T_2$ and the measured pressure value(s) Δp or $p_1$, $p_2$ a heat capacity $c_P\rho$, a calorific value Hρ or a parameter indicative thereof, a methane number MN and/or a Wobbe index WI or a parameter indicative thereof, of the fluid g with correlation functions.

The computer program may be provided in a source code, in a machine-executable code, or in any intermediate form of code-like object code. It can be provided as a computer program product on a computer-readable medium in tangible form, e.g. on a CD-ROM or on a Flash ROM memory element, or it can be made available in the form of a network-accessible medium for download from one or more remote servers through a network.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
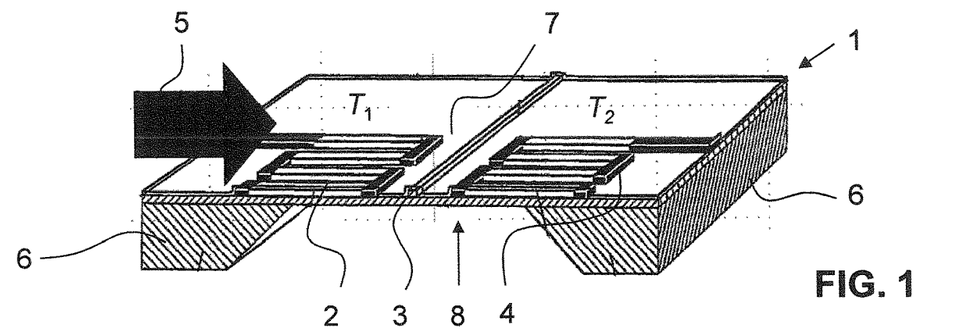
FIG. 1 shows a known thermal flow meter device.

FIG. 1 shows a perspective view of a cross section of a thermal flow sensor 1 as described, e.g., in EP 1 426 740. The thermal flow sensor 1 comprises a substrate 6 (being preferably a semiconductor substrate, preferably from silicon). The substrate 6 is etched from one side to have a recess 8, wherein said recess 8 spanned by a membrane 7. On the membrane 7 are arranged, thermally well insulated, a first temperature sensor 2, a second temperature sensor 4, the second temperature sensor 4 being arranged downstream of the first temperature sensor 2, and a heater element 3, the heater element 3 being arranged being arranged between the two temperature sensors 2, 4.

The first temperature sensor 2 measures a first temperature $T_1$, the second temperature sensor 4 a second temperature $T_2$. In the present embodiment, the temperature sensors 2, 4 are thermopiles; in other embodiments, the temperature sensors 2, 4 may be of a different type, e.g. resistive temperature sensors. Typically, the heater element 3's working principle is based on the Joule heating effect, i.e. the heater element 3 is a resistive heater.

The temperature of the heater element 3 is generally stabilized above a temperature of the substrate 6. As a fluid g overflows the heater 3, heat energy is transported from the heater element 3 to the second temperature sensor 4. Accordingly, the second $T_2$ is higher than the first $T_1$. The temperature difference $T_2-T_1$ (or, equivalently, the ratio of these temperatures) depends, inter alia, on the fluid flow 5 and on the heat transfer properties of the fluid g, in particular, on its heat conductivity and heat capacity.

This type of flow sensor 1 is described, e.g., in WO 01/98736 A1 and U.S. Pat. No. 7,188,519 B2; the disclosure of these documents is incorporated herein by reference in its entirety for teaching the setup of the flow sensor device 1.

Figure 2:
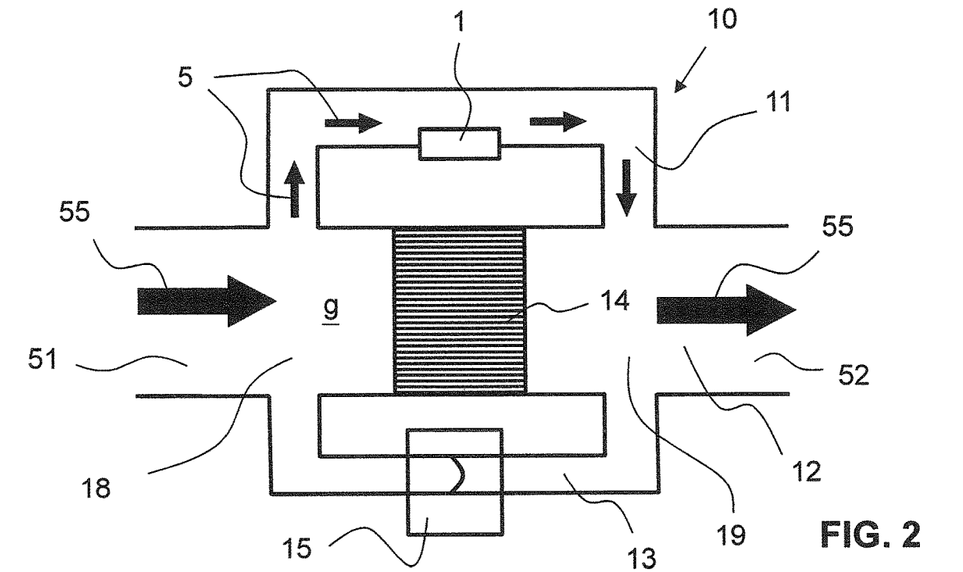
FIG. 2 shows a first embodiment of a sensor device according to invention with a main channel/by-pass channel design, wherein the thermal flow meter device according to FIG. 1 is arranged in the by-pass channel; the sensor device further comprises a laminar flow restrictor in the main-flow channel and a differential pressure sensor.

FIG. 2 shows a first preferred embodiment of a sensor device 10 according to the present invention. The sensor device 10 comprises a main-pass channel 12 carrying a main flow 55 and the first by-pass channel 11 branching off the main-pass channel 12 at a first position 18, whilst remerging back into the main-pass channel 12 at a second position 19, the second position 19 being located downstream of the first position 18. Fluid flow 55 enters through a fluid inlet 51 and exits the by-pass channel 11 through the fluid outlet 52.

The first by-pass channel 11 carries a by-pass flow 5. In the first by-pass channel 11, said thermal flow sensor 1 is arranged for measuring the fluid g conveyed through the sensor device 10. Flow meter 1 is preferably a wall-mounted sensor device. The thermal flow sensor 1 is integrated to the sensor device 10, e.g., with conventional circuitry 209 (e.g. analog amplifiers, an A/D-converter, and/or digital signal processors).

A second by-pass channel 13 is provided between the first and second positions 18, 19. In said second by-pass channel 13, a differential pressure sensor device 15 is arranged. No fluid flow is established in said second by-pass channel 13, wherein, in the first by-pass channel 11, fluid g may flow without being noticeably disturbed by the thermal flow sensor 1.

In the main-pass channel 12 is arranged, between the first and second positions 18, 19, a laminar flow restrictor 14. The flow restrictor 14 established a pressure drop Δp in the fluid g between the first and the second positions 18, 19.

Accordingly, with the differential pressure sensor device 15, the pressure difference Δp in the fluid g between positions 18, 19 and the two fluid temperatures $T_1$ and $T_2$ at positions 18 and 19, respectively, may be measured.

Figure 3:
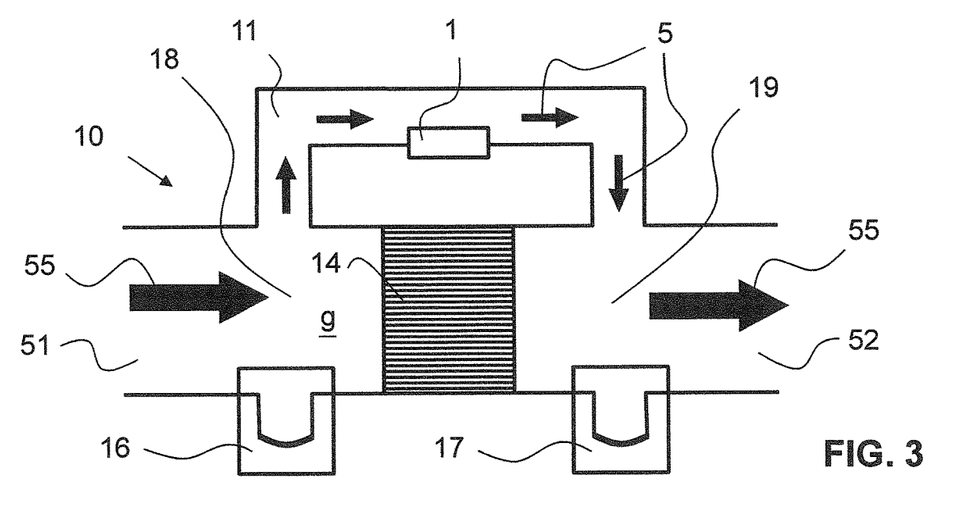
FIG. 3 shows a second embodiment of the sensor device according to invention, wherein the pressure difference is determined by means of two absolute pressure sensors arranged upstream and downstream of the flow restrictor.
Figure 4:
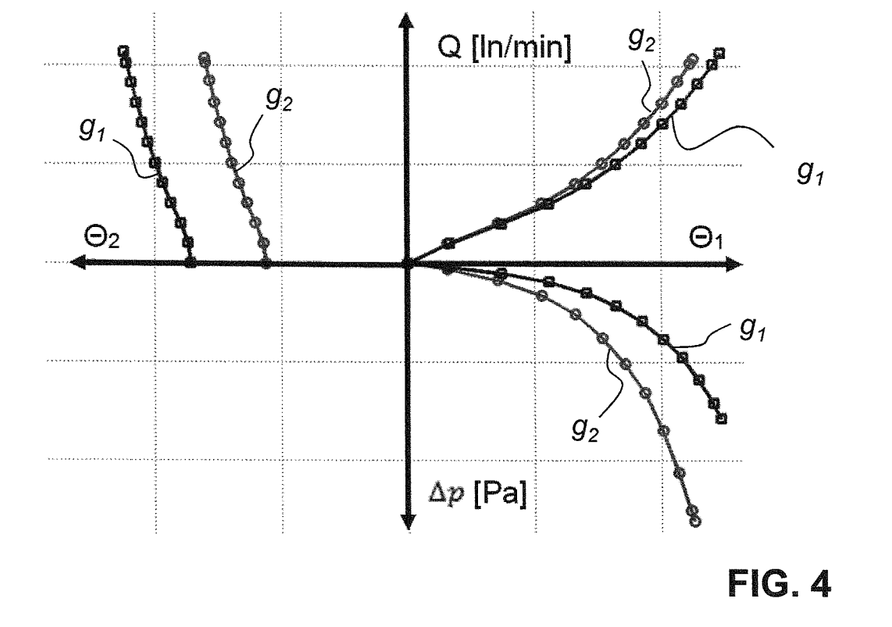
FIG. 4 shows an example of experimental data recorded for two different calibration gases.

An alternative embodiment of the sensor device 10 is depicted in FIG. 3. In this embodiment, the pressure difference Δp is not directly measured in the second by-pass channel 13, but absolute pressures $p_1$ and $p_2$ at the first and second positions 18, 19, respectively, are measured. Said absolute pressures $p_1$ and $p_2$ may be measured by means of absolute pressure sensor devices 16, 17 arranged at the first and second positions 18, 19, respectively. The pressure difference Δp is then readily obtained by $\Delta p = p_1 - p_2$.

It is to be understood that other designs of the sensor device 10 may be used. For example, the flow meter device 1 may be arranged directly in the main flow 55.

In the following, a preferred method of determining a calorific value of the unknown fluid g, in particular a natural gas (or a mixture of such gases), based on the data set Δp, $T_1$ and $T_2$ and calibration data LTU1-LUT4 is described.

The heat conductivity λ and the microscopic force ξ of the fluid g may be determined experimentally. Generally, the microscopic force ξ of the fluid g is given by $$\xi = \eta^2/(\rho Pr^{2\alpha}).$$

Here, the parameters of the fluid g are the following: η is the dynamic viscosity, ρ denotes the density, and Pr is the so-called Prandtl number $Pr = c_P\eta/\lambda$, where $c_P$ is the specific heat and λ heat conductivity of the fluid g. Parameter α is a real number in the range fluid $0 \leq \alpha \leq 1$. Typically, the sensor device 10 is operated at temperature of −40° C. to 150° C. and at pressures of 0.01 MPa to 1 MPa.

Now, in a first step, the heat conductivity λ of the fluid g may be determined from the two independent temperature $T_1$ and $T_2$ signals obtained by means of the thermal flow sensor 1. The $T_1$ and $T_2$ signals depend on the flow velocity v of the fluid g and on physical parameters of the fluid g as follows:

$$T_i = F_i(c_P \rho v/\lambda, \lambda, Pr) \text{ with } i=1,2. \quad (1)$$

The functions $F_i(c_P \rho \xi/\lambda, \lambda, Pr)$ in Eq. (1) depend on the details of the measurement setup (e.g. the geometry of the main-pass/by-pass channel system, flow restrictors . . . ) as well as on the design and location of thermal flow sensor 1 in the by-pass channel 11. The functional dependence of Eq. (1) follows from the heat equation.

Generally, the heat conductivity λ of the fluid g is given as:

$$\lambda = f(T_1, T_2). \quad (2)$$

The function $f(T_1, T_2)$ in Eq. (2) can be determined, for example, through calibration measurements.

Let $\Theta_1 = T_2 - T_1$ and $\Theta_2 = T_1 + T_2$. It is noted that, in other embodiments, other linear combinations of $T_1$ and $T_2$ signals may be used.

Two calibration gases $g_1$ and $g_2$ with known heat conductivities $\lambda^{g1}$ and $\lambda^{g2}$, respectively, may be measured in calibration measurements. One sends both fluids $g_1$ and $g_2$, one at a time, through the sensor device 10 and varies the volume flow Q in the relevant flow range to determine the curves or sets of value pairs $\Theta_2^{g1}(\Theta_1^{g1})$ for fluid $g_1$ and $\Theta_2^{g2}(\Theta_1^{g2})$ for fluid $g_2$.

By measurement of the fluid g, one determines its heat conductivity λ by means of linear interpolation of the $\Theta_2$ signal while keeping the $\Theta_1$ signal constant:

$$\lambda = x\lambda^{g1} + (1-x)\lambda^{g2}, \quad (3)$$

with $$x = [\Theta_2 - \Theta_2^{g2}(\Theta_1)]/[\Theta_2^{g1}(\Theta_1) - \Theta_2^{g2}(\Theta_1)]. \quad (4)$$

Instead of using two calibration fluids $g_1$ and $g_2$ one may also use master data and calibration data from only one calibration fluid. In this case, the thermal conductivity is determined from the relation $\lambda = \lambda^{g1} + m(\Theta_1)[\Theta_2 - \Theta_2^{g1}(\Theta_1)]$, where the slope $m(\Theta_1)$ was determined beforehand by averaging calibration data (with two calibration gases) of many sensors. Said slope may be the master data.

Preferably, the data is averaged over a plurality of single measurements. The single measurements may be performed at different values for the fluid flow Q.

Figure 7:
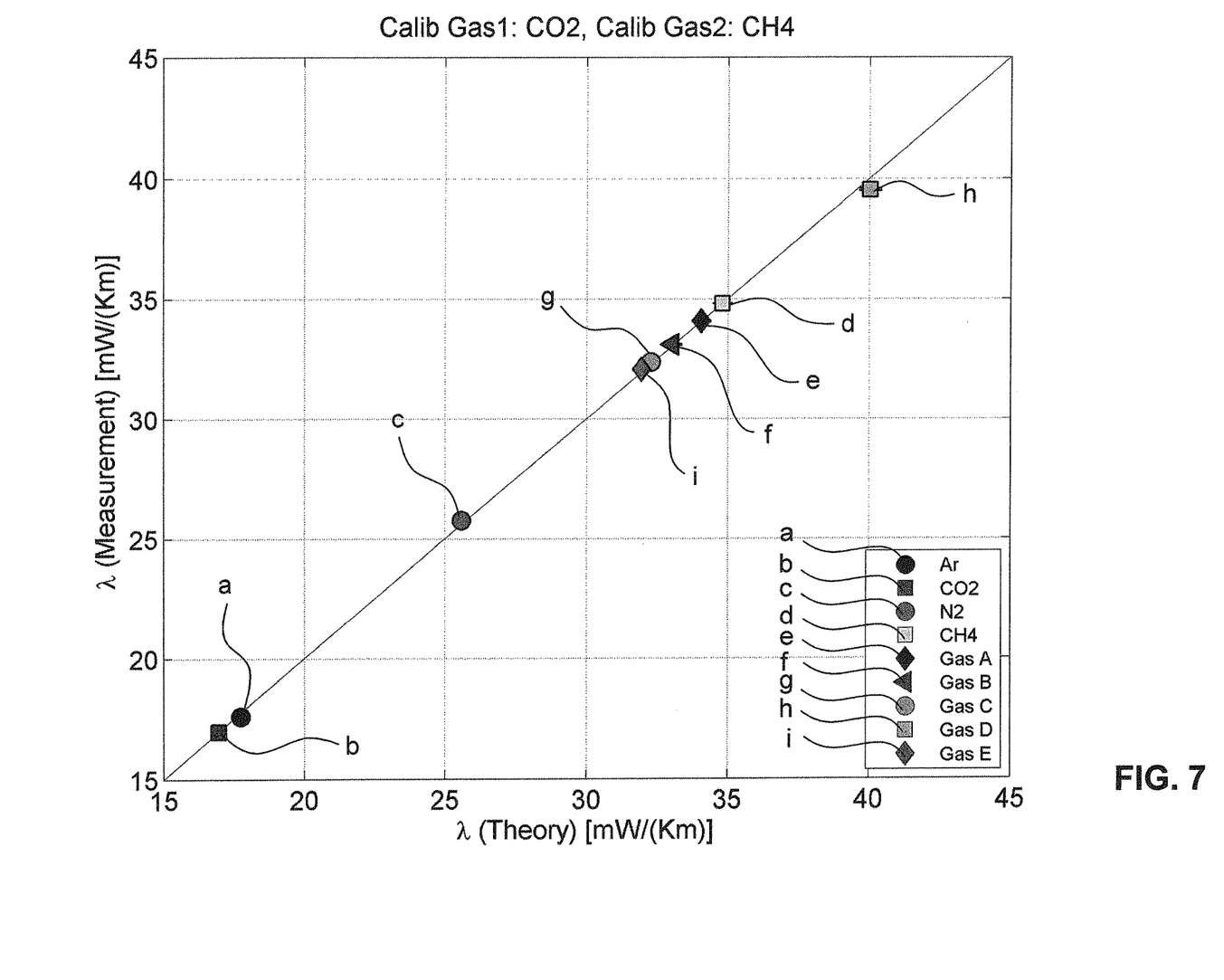
FIG. 7 shows a correlation between heat conductivity measurements and theory as presented herein.

FIG. 7 shows heat conductivity λ measurements with the calibrated sensor device 10 with a plurality of gases a-i. The data has been average over several data sets recorded at different fluid flow values Q. The two calibration gases are $CO_2$ and $CH_4$. In a next step, the microscopic force ξ of the fluid g may be determined from the first and second temperature $T_1$ and $T_2$ signals and the pressure difference Δp signal obtained from the pressure sensors device 15 or 16, 17:

$$\xi = g(\Theta_1, \Theta_2, \Delta p). \quad (5)$$

By means of the pressure sensor device 15 or 16, 17 the differential pressure Δp is measured. The differential pressure Δp depends on the flow velocity ξ as well as on the physical parameter η and ρ of the flowing fluid g as follows:

$$\xi = \eta^2/\rho * H(\rho v/\eta), \quad (6)$$

wherein the function $H(\rho\xi/\eta)$ depends on the details of the measurement setup (e.g. the geometry of the main-pass/by-pass channel system, flow restrictors . . . ). The functional dependence of Eq. (6) on the fluid parameters follows from the similarity transformation of the Navier-Stokes equations for incompressible fluids.

The function $g(\Theta_1, \Theta_2, \Delta p)$ may be determined by means of calibration measurements. Let $\Theta_1 = T_2 - T_1$ and $\Theta_2 = T_1 + T_2$. Again, it is possible to use other linear combinations of the $T_1$ and $T_2$ signals.

For the calibration measurements, the two calibration gases $g_1$ and $g_2$ are used again, wherein the microscopic force parameters $\xi^{g1}$ and $\xi^{g2}$ of both gases $g_1$ and $g_2$ are known. During the calibration measurements, the fluid flow Q is varied in the relevant flow range, i.e. in the range the sensor device 10 shall operate with fluid g, and the two independent $T_1$ and $T_2$ signals obtained by means of the thermal flow sensor 1 and the differential pressure Δp is obtained by means of the pressure sensor device 15 or 16, 17. From these data, the two curves or sets of value pairs $\Delta p^{g1}(\Theta_1^{g1})$ for the first calibration gas $g_1$ and $\Delta p^{g2}(\Theta_1^{g2})$ for the second calibration gas $g_2$ are determined.

During use, the gas g is measured by means of the thermal flow sensor 1 and the pressure sensor device 15 or 16, 17. From the thermal flow sensor $\Theta_1$ and $\Theta_2$ are obtained. On the basis of the $\Theta_1$ and $\Theta_2$ data, rescaled parameters $\Theta_1'$ and $\Theta_1''$ are calculated.

$\Theta_1'$ and $\Theta_1''$ are the rescaled $\Theta_1$ parameters which are chosen such that the heat conductivity value λ corresponds to the heat conductivity values $\lambda^{g1}$ and $\lambda^{g2}$ of the calibration gases $g_1$ and $g_2$, respectively. Accordingly, $\Theta_1 = F_1(c_P\rho\xi/\lambda, \lambda Pr) \rightarrow \Theta_1' = F_1(c_P\rho\xi/\lambda, \lambda^{g1}, Pr)$ and $\Theta_1 = F_1(c_P\rho\xi/\lambda, \lambda, Pr) \rightarrow \Theta_1'' = F_1(c_P\rho\xi/\lambda, \lambda^{g2}, Pr)$. In this way, the explicit dependency of the $\Theta_1$ and $\Theta_2$ data on λ is removed.

Then, the microscopic force $\xi$ is given by the linear interpolation formula:

$$\xi = w\xi^{g1} + (1-w)\xi^{g2} \qquad (7)$$

with $$w = [\Delta p - \Delta p^{g2}(\Theta_1'')]/[\Delta p^{g1}(\Theta_1') - \Delta p^{g2}(\Theta_1'')]. \qquad (8)$$

The rescaled sensor signals $\Theta_1'$ and $\Theta_1''$ in Eq. (8) may be determined as follows. By means of Eqs. (3, 4), one first determines the heat conductivity $\lambda$ of the unknown gas g as outlined above. If said heat conductivity $\lambda$ is close enough to $\lambda^{g1}$ and $\lambda^{g2}$ the $\Theta_1$ sensor signal may be linearized in parameter $\lambda$ as follows:

$$\Theta_1 = u\Theta_1^{g1}(\phi) + (1-u)\Theta_1^{g2}(\phi) \qquad (9)$$

with $$u = (\lambda - \lambda^{g2})/(\lambda^{g1} - \lambda^{g2}). \qquad (10)$$

Here, $\phi = c_P \rho \xi/\lambda$. Said heat conductivity $\lambda$ being "close enough" to $\lambda^{g1}$ and $\lambda^{g2}$ means that $\lambda$ is in the range with a lower bound of 50% to 125%, preferably 80% to 100% of the smaller of $\lambda^{g1}$ and with an upper bound of 100% to 150%, preferably 125% of the larger of $\lambda^{g1}$ and $\lambda^{g2}$, preferably it means that $\lambda^{g1} \leq \lambda \leq \lambda^{g2}$, wherein $\lambda^{g1}$ and $\lambda^{g2}$ differ by not more than 20% of the larger one of both.

For given sensor signals $\Theta_1$ and $\Theta_2$, Eq. (9) implicitly defines the parameter $\phi = \phi(\Theta_1, \Theta_2)$. From said parameter $\phi$ one can calculate the rescaled sensor signals $\Theta_1' = \Theta_1^{g1}(\phi(\Theta_1, \Theta_2))$ and $\Theta_1'' = \Theta_1^{g2}(\phi(\Theta_1, \Theta_2))$.

Preferably, the data is averaged over a plurality of single measurements. The single measurements may be performed at different values for the fluid flow Q.

Figure 8:
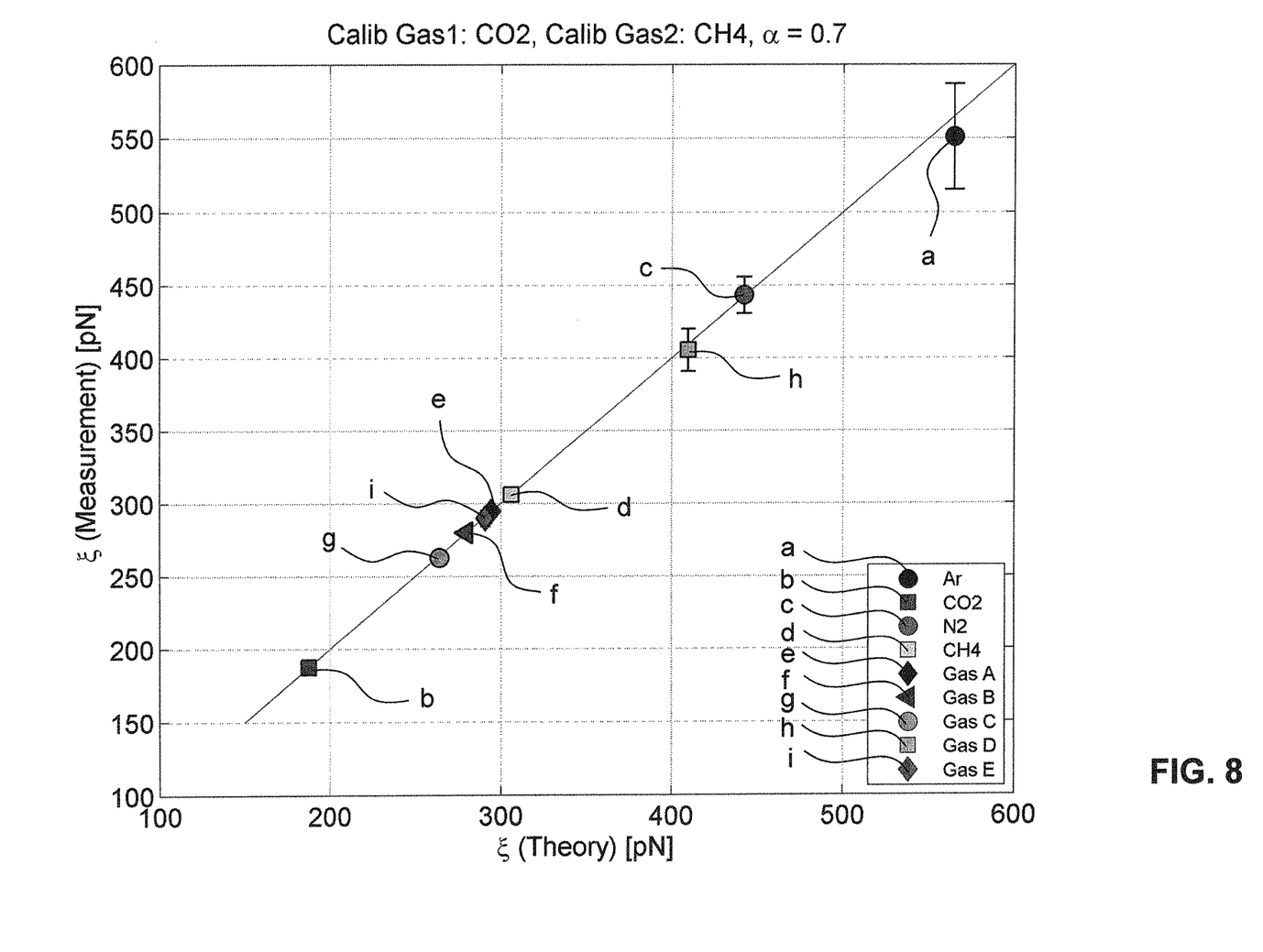
FIG. 8 shows a correlation between microscopic force measurements and theory as presented herein.

FIG. 8 shows microscopic force $\xi$ measurements with the calibrated sensor device 10 with a plurality of gases a-i. The data has been average over several data sets recorded at different fluid flow values. The two calibration gases are $CO_2$ and $CH_4$.

If one uses master data, $\phi(\Theta_1, \Theta_2)$ may be determined by measurement of one calibration gas only. In this case, Eq. (9) may be replaced by $\Theta_1 = [1 + q(\phi)(\lambda - \lambda^{g1})]\Theta_1^{g1}(\phi)$ where the slope $q(\phi)$ has been determined beforehand by averaging over the calibration data (with at least two calibration gases) of many sensors. Said slope may be used as master data.

This method may be used for providing, e.g., an energy meter, e.g., for burnable gases such as natural gases. Generally, an energy meter determines a volume flow and the energy specific parameters such as calorific value H$\rho$ or Wobbe index WI (in energy per volume) of an unknown burnable gas.

Accordingly, the sensor device 10 may be configured for measuring $T_1$, $T_2$ and $\Delta p$ of the fluid g. Moreover, fluid measurement device may comprise a digital control circuit 20 configured for carrying out the method as outlined above.

Figure 5:
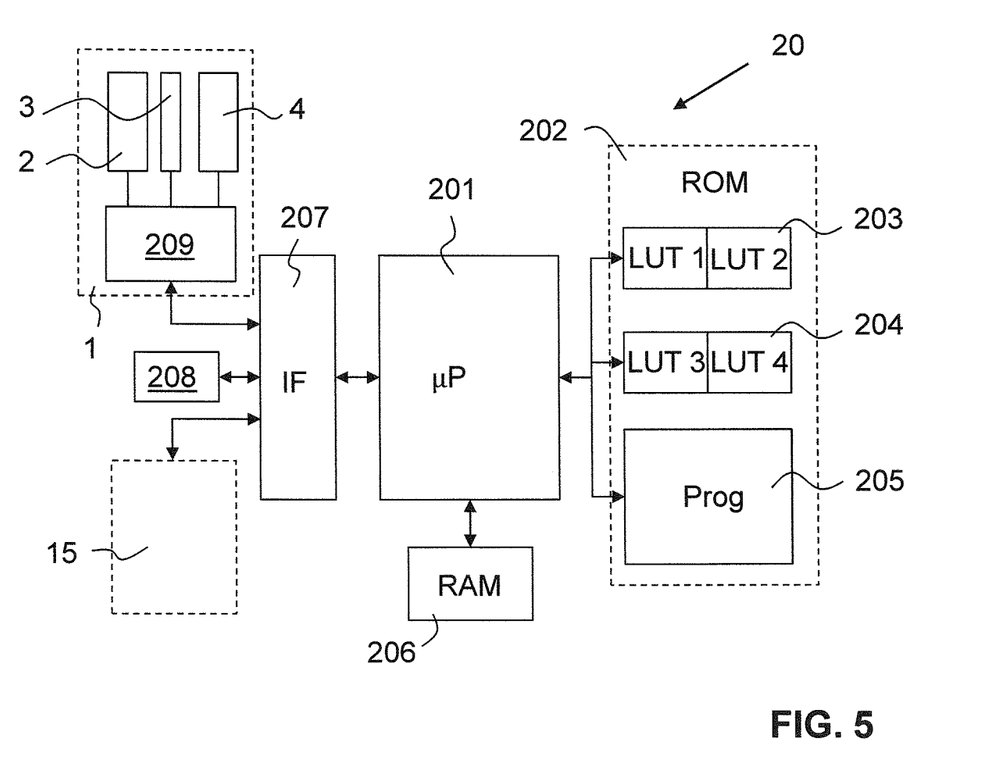
FIG. 5 shows a simplified block diagram of a digital control circuit for the sensor device according to FIG. 2 or FIG. 3.

FIG. 5 shows a schematic block diagram of the digital control circuit 20 for sensor device 10. The control circuit 20 comprises a processor unit (CPU, μP) 201, a non volatile (e.g. a Flash ROM) memory 202, and a volatile (RAM) memory 206. The processor 201 communicates with the memory modules 202, 206. The nonvolatile memory 202 stores, inter alia, a plurality of sets of calibration data 203, 204 in the form of lookup tables LUT1-LUT4, as well as a machine-executable program 205 for execution in the processor 201. Lookup table LUT1 includes calibration data $\Theta_2^{g1}(\Theta_1^{g1})$ and lookup table LUT3 the calibration data $\Delta p^{g1}(\Theta_1^{g1})$ from the first calibration gas $g_1$ and lookup table LUT2 comprises calibration data $\Theta_2^{g2}(\Theta_1^{g2})$ and lookup table LUT4 the calibration data $\Delta p^{g2}(\Theta_1^{g2})$ related to the second calibration $g_2$. LUT1 and LUT3 also include the heat conductivity parameters $\lambda^{g1}$ and $\lambda^{g2}$ and LUT2 and LUT4 the microscopic force parameters $\xi^{g1}$ and $\xi^{g2}$ and of both calibration gases $g_1$ and $g_2$, respectively.

Via a data interface 207, the processor 201 communicates with various peripherals, including the thermal flow sensor 1, the differential pressure sensor device 15 (or, in the embodiment according to FIG. 3, absolute pressure sensor devices 16, 17), and a user interface 208 (which may include, e.g., at least one of a network interface for interfacing with an external input/output device, a dedicated input device such as a keyboard and/or mouse, and a dedicated output device, such as e.g. an LCD screen).

Figure 6:
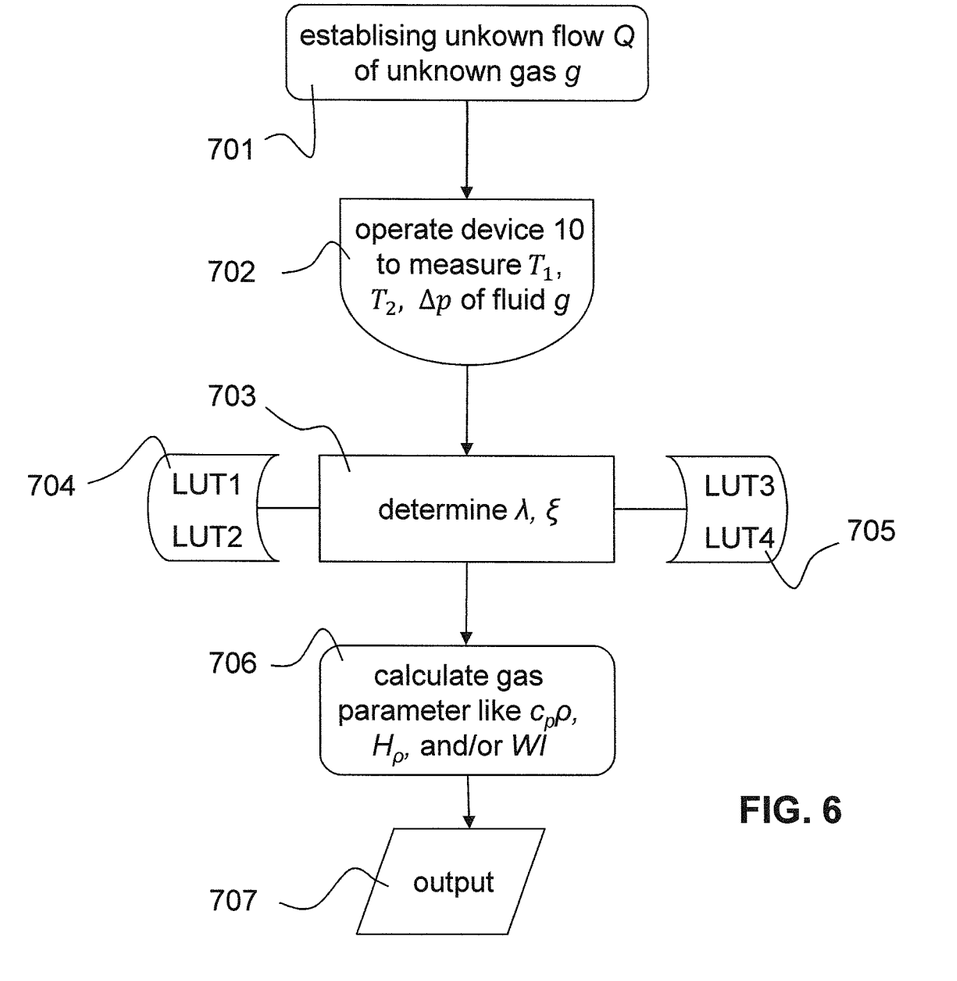
FIG. 6 shows a flow diagram of a method according to a first embodiment of the present invention.

FIG. 6 depicts how the sensor device 10 may be operated for determining an energy transport per time unit of the fluid g. In step 701, a constant, unknown fluid flow Q (in the measurement range of the sensor device 10) of the unknown fluid g is set. In step 702, the control unit 20 commands the sensor device 10 to measure $T_1$, $T_2$ and $\Delta p$. In step 703, the control unit 20 uses in steps 704 and 705 the lookup tables 203 (LUT1, LUT3) for the first calibration gas $g_1$ and 204 (LUT2, LUT4) for the second calibration gas $g_2$, respectively, for calculating the heat conductivity $\lambda$ and the microscopic force $\xi$ of the unknown fluid g as outlined above. In a next step 707, correlation functions (see Eq. 11 below) that are stored in the ROM 202 are used for calculation of the heat capacity $c_P \rho$, the calorific value H$\rho$, the methane number MN, and/or the Wobbe index WI.

Moreover, by means of the heat capacity $c_P \rho$ and heat conductivity $\lambda$ the volume flow Q of the unknown gas g may be determined using the equation above. In combination with the calorific value H$\rho$ one can obtain the energy transport per time unit.

The correlation functions between the fluid parameters may be found by regression analysis. One may analyze e.g. a large data set containing physical properties of burnable gases or mixtures thereof. Such data sets are publicly available, e.g. in the report "Report on gas composition range in Europe" (available under http://www.ingas-eu.org/docs/DB0.1.pdf).

Moreover, if the composition of the burnable gas, in particular the natural gas is known, physical parameters relevant here may be calculated by means of commercially available programs such as Refprop NIST (available under http://www.nist.gov/srd/nist23.cfm) or PPDS (available under http://www.tuv-sud.co.uk/uk-en/about-tuev-sued/tuev-sued-in-the-uk/nel/ppds-thermodynamic-properties-suite).

The correlations functions for a quadratic Ansatz may be written as:

$$c_P \rho = A_1 + B_1 \lambda + C_1 \lambda^2 + D_1 \xi + E_1 \xi^2 + F_1 \lambda \xi$$

$$H\rho = A_2 + B_2 \lambda + C_2 \lambda^2 + D_2 \xi + E_2 \xi^2 + F_2 \lambda \xi$$

$$WI = A_3 + B_3 \lambda + C_3 \lambda^2 + D_3 \xi + E_3 \xi^2 + F_3 \lambda \xi \qquad (11)$$

Using the least squares method, one may obtain the coefficients $A_i$ to $F_i$, i=1 to 3. The following set of coefficients was found (Tab. 1):

| $\alpha = 0.7$ | $A_i$ | $B_i$ | $C_i$ | $D_i$ | $E_i$ | $F_i$ |
|---|---|---|---|---|---|---|
| $c_P \rho$ [kJ/(Km$^3$)], i = 1 | 2.792 | −0.156 | 0.026 | −1.869 | 0.616 | 0.047 |

-continued

| $\alpha = 0.7$ | $A_i$ | $B_i$ | $C_i$ | $D_i$ | $E_i$ | $F_i$ |
|---|---|---|---|---|---|---|
| $H\rho$ [MJ/m$^3$], i = 2 | −59.26 | 352.80 | −188.44 | −162.98 | 28.51 | 65.34 |
| WI [MJ/Sm$^3$], i = 3 | −142.46 | 528.28 | −223.47 | −190.63 | 44.90 | 36.71 |

Here, the coefficients $A_i$ to $F_i$, i=1 to 3 are normalized such that the heat conductivity $\lambda$ an the microscopic force $\xi$ are given with reference to the heat conductivity $\lambda$ an the microscopic force $\xi$ of methane. For the calculation of $\xi$ the value $\alpha=0.7$ was used.

The standard deviation of the relative error of the fit using the coefficients $A_i$ to $F_i$, i=1 to 3 of Tab. 1 was found to be 0.28% for $c_P\rho$, 0.15% for $H\rho$, and 0.43% for WI.

An illustrative set of exemplary values is given in Tabs. 2, 3, 4, wherein all values are calculated at temperature T=25° C. and pressured p=0.1 MPa.

Theoretical values as calculated by said commercially available programs (Tab. 2):

| | $\lambda$ [mW/(Km)] | $\xi$ ($\alpha = 0.7$) [nN] | $c_P\rho$ [kJ/(Km$^3$)] | $H\rho$ [MJ/m$^3$] | WI [MJ/(Sm$^3$)] |
|---|---|---|---|---|---|
| methane | 34.82 | 306.0 | 1.452 | 35.99 | 53.45 |
| gas 1 | 32.04 | 260.1 | 1.557 | 39.08 | 53.82 |
| gas 2 | 32.76 | 302.9 | 1.465 | 33.36 | 46.29 | wherein gas 1 and gas 2 have the following compositions (Tab. 3):

| | methane | nitrogen | ethane | propane | carbon dioxide |
|---|---|---|---|---|---|
| gas 1 | 85.9% | 1.0% | 8.5% | 3.1% | 1.5% |
| gas 2 | 84.4% | 10.4% | 2.6% | 1.5% | 1.1% |

Values calculated by means of correlation function, i.e. Eqs. (11) (Tab. 4):

| | $c_P\rho$ corr [kJ/(Km$^3$)] | $H\rho$ corr [MJ/m$^3$] | WI corr [MJ/(Sm$^3$)] |
|---|---|---|---|
| methane | 1.456 | 35.97 | 53.33 |
| gas 1 | 1.563 | 38.99 | 53.55 |
| gas 2 | 1.466 | 33.32 | 46.24 |

From the Wobbe index one may determine the methane number MN.

Accordingly, the present invention provides a small, inexpensive sensor element 10 and an inexpensive method which may be used for determining fluid parameters, wherein a pressure drop over the flow restrictor of maximum 2 millibars, as required by the relevant norm, is complied with.

| LIST OF REFERENCE SIGNS | |
|---|---|
| 1 | thermal flow sensor device |
| 2 | first temperature sensor on 1 |
| 3 | heater element on 1 |
| 4 | second temperature sensor on 1 |
| 5 | by-pass flow of fluid g |
| 6 | substrate of 1 |
| 7 | membrane on 6 |
| 8 | recess in 6 |

-continued

| LIST OF REFERENCE SIGNS | |
|---|---|
| 10 | sensor device |
| 11 | first by-pass channel |
| 12 | main-pass channel |
| 13 | second by-pass channel |
| 14 | flow restrictor in 12 |
| 15 | differential pressure sensor device |
| 16, 17 | absolute pressure sensor device |
| 18 | first position |
| 19 | second position |
| 20 | control circuit |
| 201 | processor unit |
| 202 | non-volatile memory |
| 203, 204 | sets of calibration data |
| 205 | machine-executable program |
| 206 | volatile memory |
| 207 | data interface |
| 208 | user interface |
| 209 | conventional circuitry |
| 51 | inlet for fluid g |
| 52 | outlet for fluid g |
| 55 | total fluid flow fluid g |
| 701 | flow establishing step |
| 702 | operating step |
| 703 | determining step |
| 704, 705 | retrieving step |
| 706 | calculating step |
| 707 | outputting step |

The invention claimed is:

1. A method for determining a characteristic parameter of a fluid, said fluid flowing in a fluid flow through a sensor device, the sensor device comprising:
    a thermal flow sensor device with a heater element and at least one temperature sensor,
    a flow restrictor arranged between first and second positions in said fluid flow, and
    a pressure sensor device for determining a pressure difference in the fluid between said first and second positions,
    the method comprising:
    (i) establishing the fluid flow with an unknown value through said sensor device with at least part of the fluid overflowing said thermal flow sensor;
    (ii) activating the heating element of said thermal flow sensor and measuring at least one first temperature with said at least one temperature sensor and at least one second temperature;
    (iii) measuring first and second absolute pressures in the fluid at the first and second positions, respectively, or measuring a differential pressure in the fluid between the first and second positions with said pressure sensor device; and
    (iv) determining from the measured first and second temperatures and calibration data a heat conductivity of said fluid of the fluid;
    (v) determining from the measured first and second temperatures, the measured pressure value(s) and calibration data a microscopic force of the fluid;
    (vi) determining from said heat conductivity and microscopic force said characteristic parameter of the fluid with correlation functions, the characteristic parameter being selected from the group consisting of the heat capacity, the calorific value and a parameter indicative thereof, the methane number, and the Wobbe index and a parameter indicative thereof.

2. The method according to claim 1, wherein the thermal flow sensor device comprises first and second temperature sensors for determining the first and second temperatures, wherein the heater element is arranged between said first and second temperature sensors.

3. The method according to claim 2, wherein the microscopic force is determined by rescaling at least part of the relevant calibration data prior to interpolation or wherein the measurement of the fluid is performed at several fluid flow values and the determined fluid parameter averaged.

4. The method according to claim 1, wherein the calibration data comprises first calibration data and second calibration data, the first and second calibration data comprising first and second temperatures and the pressure value(s) for at least one calibration fluid, wherein the first and second calibration data is stored in at least one lookup table, and wherein said heat conductivity and said microscopic force are determined by interpolation of the respective calibration data.

5. The method according to claim 4, wherein the first calibration data comprise the heat conductivity of the at least one calibration fluid and the second calibration data comprise the microscopic force of the at least one calibration fluid.

6. The method according to claim 1, wherein the correlation functions are based on a quadratic Ansatz.

7. The method according to claim 1, further comprising:
(vii) determining a volume flow of the fluid flow of the fluid from the heat capacity and the heat conductivity determined previously.

8. The method according to claim 7, further comprising:
(viii) determining an energy transfer per time unit from the volume flow and the calorific value of the fluid.

9. The method according to claim 1, further comprising:
(ix) outputting the heat capacity, the calorific value, the Wobbe index, the methane number, an energy transfer determined from the volume fluid and the calorific value of the fluid, or a parameter indicative of any one thereof.

10. The method according to claim 1, wherein the fluid or the at least one calibration fluid is a burnable gas or a mixture thereof, or a natural gas or a mixture thereof.

11. The method according to claim 1, wherein first calibration data and second calibration data comprise first and second temperatures and the pressure value(s) for at two calibration fluids, wherein the first and second calibration data is stored in at least one lookup table, and wherein said heat conductivity and said microscopic force are determined by interpolation of the respective calibration data.

12. A sensor device for measuring a characteristic parameter selected from the group consisting of a heat capacity, a calorific value, a methane number, and a Wobbe index of a fluid, or a parameter indicative of any one thereof, the sensor device comprising:
a flow channel for the fluid, the flow channel having an inlet and an outlet for the fluid,
a thermal flow sensor device with a heater element and two temperature sensors and the heater element arranged therebetween,
a flow restrictor arranged between first and second positions in said flow channel,
at least one pressure sensor device for determining a pressure difference in the fluid between said first and second positions,
and a digital control circuit comprising a memory,
wherein the digital control circuit is configured to carry out a method comprising:
(i) establishing the fluid flow with an unknown value through said sensor device with at least part of the fluid overflowing said thermal flow sensor;
(ii) activating the heating element of said thermal flow sensor and measuring at least one first temperature with said at least one temperature sensor and at least one second temperature;
(iii) measuring first and second absolute pressures in the fluid at the first and second positions, respectively, or measuring a differential pressure in the fluid between the first and second positions with said pressure sensor device; and
(iv) determining from the measured first and second temperatures and calibration data a heat conductivity of said fluid of the fluid;
(v) determining from the measured first and second temperatures, the measured pressure value(s) and calibration data a microscopic force of the fluid;
(vi) determining from said heat conductivity and microscopic force said characteristic parameter of the fluid with correlation functions, the characteristic parameter being selected from the group consisting of the heat capacity, the calorific value and a parameter indicative thereof, the methane number, and the Wobbe index and a parameter indicative thereof.

13. The sensor device according to claim 12, wherein a memory is configured to store first and second calibration data, and wherein the digital control circuit is configured to retrieve the first and second calibration data from said memory and to determine the characteristic parameter.

14. The sensor device according to the claim 12, wherein the thermal flow sensor device is a CMOS flow sensor device.

15. The sensor device according to claim 13, wherein the correlations functions are stored in said memory.

16. The sensor device according to claim 13, wherein the digital control circuit is configured to determine the heat capacity, the calorific value or the parameter indicative thereof, the methane number or the parameter indicative thereof, or a Wobbe index or the parameter indicative thereof, of the fluid with said correlation functions.

17. A non-transitory computer usable memory medium having a computer readable program code embodied therein for execution by a digital control circuit of a sensor device, said sensor device comprising:
a flow channel for the fluid, the flow channel having an inlet and an outlet for the fluid,
a thermal flow sensor device with a heater element and two temperature sensors and the heater element arranged therebetween,
a flow restrictor arranged between first and second positions in said flow channel,
at least one pressure sensor device for determining a pressure difference in the fluid between said first and second positions,
wherein, when executed by the digital control circuit, the program code implements a method comprising:
(i) establishing the fluid flow with an unknown value through said sensor device with at least part of the fluid overflowing said thermal flow sensor;
(ii) activating the heating element of said thermal flow sensor and measuring at least one first temperature with said at least one temperature sensor and at least one second temperature;
(iii) measuring first and second absolute pressures in the fluid at the first and second positions, respectively, or measuring a differential pressure in the fluid between the first and second positions with said pressure sensor device; and
(iv) determining from the measured first and second temperatures and calibration data a heat conductivity of said fluid of the fluid;
(v) determining from the measured first and second temperatures, the measured pressure value(s) and calibration data a microscopic force of the fluid;
(vi) determining from said heat conductivity and microscopic force said characteristic parameter of the fluid with correlation functions, the characteristic parameter being selected from the group consisting of the heat capacity, the calorific value and a parameter indicative thereof, the methane number, and the Wobbe index and a parameter indicative thereof.

18. A method for determining a characteristic parameter of a fluid, said fluid flowing in a fluid flow through a sensor device, the sensor device comprising:
a thermal flow sensor device with a heater element and at least one temperature sensor,
a flow restrictor arranged between first and second positions in said fluid flow, and
a pressure sensor device for determining a pressure difference in the fluid between said first and second positions,
the method comprising:
(i) establishing the fluid flow with an unknown value through said sensor device with at least part of the fluid overflowing said thermal flow sensor;
(ii) activating the heating element of said thermal flow sensor and measuring at least one first temperature with said at least one temperature sensor and at least one second temperature;
(iii) measuring first and second absolute pressures in the fluid at the first and second positions, respectively, or measuring a differential pressure in the fluid between the first and second positions with said pressure sensor device; and
(iv) determining from the measured first and second temperatures and calibration data a heat conductivity of said fluid of the fluid;
(v) determining from the measured first and second temperatures, the measured pressure value(s) and calibration data a microscopic force of the fluid, wherein the microscopic force of the fluid is given by $$\xi=\eta^2/(\rho Pr^{2\alpha}), \text{ with}$$

$\eta$ being the dynamic viscosity, $\rho$ the density, and Pr the Prandtl number $Pr=c_P\eta/\lambda$, where $c_P$ is the specific heat and $\lambda$ the heat conductivity of the fluid, and parameter $\alpha$ being a real number in the range fluid $0\leq\alpha\leq1$;
(vi) determining from said heat conductivity and microscopic force said characteristic parameter of the fluid with correlation functions, the characteristic parameter being selected from the group consisting of the heat capacity, the calorific value and a parameter indicative thereof, the methane number, and the Wobbe index and a parameter indicative thereof.

* * * * *